United States Patent [19]

Kater

[11] Patent Number: 4,535,786
[45] Date of Patent: Aug. 20, 1985

[54] MEASUREMENT OF BODY FLUID CHEMISTRY

[76] Inventor: John A. R. Kater, 2037 W. San Lorenzo, Santa Ana, Calif. 92704

[21] Appl. No.: 516,627

[22] Filed: Jul. 25, 1983

[51] Int. Cl.³ .............................................. G01N 27/46
[52] U.S. Cl. .................................... 128/760; 128/630; 604/4; 204/403
[58] Field of Search ............... 128/630, 632, 637, 760; 436/68, 150; 422/68; 204/403, 411; 604/4–6

[56] References Cited

U.S. PATENT DOCUMENTS

| | | | |
|---|---|---|---|
| 3,556,950 | 1/1971 | Dahms | 422/68 X |
| 3,910,256 | 10/1975 | Clark et al. | 604/4 X |
| 3,997,420 | 12/1976 | Buzza | 204/411 |
| 4,109,505 | 8/1978 | Clark et al. | 204/403 X |
| 4,202,747 | 5/1980 | Buzza et al. | 204/411 |
| 4,318,885 | 3/1982 | Suzuki et al. | 422/68 |

OTHER PUBLICATIONS

Walton, D. M. et al., "Continuous Monitoring of Blood pH, PCO₂ and PO₂ in Clinical Practice", Conference 8th ISA Biomedical Sciences International Symposium, Denver, Colorado U.S.A. (May 4-6 1970) pp. 155-158.

*Primary Examiner*—Edward M. Coven
*Attorney, Agent, or Firm*—Grover A. Frater

[57] ABSTRACT

A method and apparatus are disclosed in which body fluid chemistry is measured in either differential or nondifferential mode using apparatus of the kind employed in infusing fluids into patients' blood streams, either with or without combination with such infusion, to the end that measurement of body fluid chemistry is conveniently and measured automatically at selected frequency.

10 Claims, 5 Drawing Figures

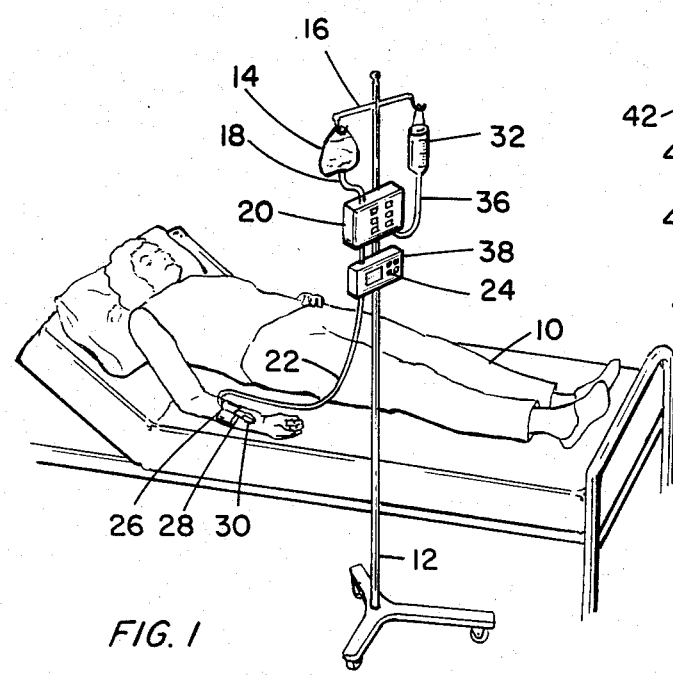

MEASUREMENT OF BODY FLUID CHEMISTRY

TECHNICAL FIELD

This invention relates to improvements in measurement of body fluid chemistry, and it relates in particular to methods and means for making automated, in-line measurements of blood and urine chemistry.

BACKGROUND ART

The ability to measure the blood electrolytes and blood gases on demand, at bedside, greatly enhances the successful management of the critically ill patient. It is common practice to make in vitro (stat) measurements of the blood electrolytes Na, K, and Ca, and blood gases including pO2, pCO2 and pH in a central or satellite laboratory. During critical stages of the patient, while in surgery, the emergency room or the intensive care unit, the physician has frequent need for the patient's electrolyte and blood gas status. Such a request is made by calling the central or satellite laboratory. The laboratory will send a technologist to collect two blood samples from the patient. These samples are collected anaerobically, placed in an ice bath, and taken to the laboratory. Upon arrival in the laboratory, the samples are entered in the log book and subjected to sample preparation, which includes such procedures as centrifugation and dilution of the serum, so obtained, for analysis.

The analysis of the electrolytes and the blood gases is done according to two distinct procedures and on two separate instruments. For blood gas analysis, an aliquot of whole blood is drawn from one of the samples and introduced into a blood gas analyzer. Any transfer of blood sample must follow careful anaerobic techniques to prevent shifting of the blood gas values due to sample handling procedures. Equally critical is the calibration procedure of the pO2, pCO2 and pH electrodes for the blood gas measurement. These electrodes are calibrated on a tonometer, where they are exposed to a liquid and/or gas phase, having a known partial pressure of O2 and CO2. This process is time consuming. Electrolytes are measured with an instrument which may use ion selective electrodes, flame photometry or atomic absorption techniques. Considering the sampling, sample preparation, calibration, measurement, and logging of the results, the physician may have to wait fifteen to forty-five minutes to get the values for a diagnostic decision. During critical care, shifts in electrolyte and blood gas values can happen rapidly, as a result of or resulting into significant physiologic events, which may endanger the patient. It is for these reasons that the ability to make bedside measurements of the blood electrolytes and blood gases, on demand, will significantly contribute to the successful management of the critically ill.

One form of in-line measurement of the blood electrolytes reported in the literature is to continuously remove a small volume of blood from the patient. The point of blood withdrawal may be a connector in a by-pass line between the patient and the heart-lung machine, or an intravenous line directly from the patient. A pump controlled test sequence alternately exposes the measuring electrodes to calibrant solution, blood and flushing solution. In this system the blood, after being measured, is discarded and not returned to the patient. This system also requires that the sampling line at the point of entry to the patient's blood stream is regularly flushed with a heparinized saline solution to prevent clot formation. The process of clot prevention is accomplished by flushings, in-line calibration, and measurement is complex.

The measurement of the chemistry of other body fluids, principally urine, also has been slow and inconvenient and costly. Even less progress has been made in the prior art to a solution to the problem of measuring the chemistry of these fluids.

DISCLOSURE OF INVENTION

An object of the invention is to provide improved methods and means for measuring the chemistry of body fluids and one specific object of the invention is to provide improved methods and means for blood electrolytes such as sodium, potassium, calcium and pH and the blood gases pO2 and pCO2.

The invention simplifies the programmed, in vivo sequential process of calibration, sampling, measurement and flushing. It provides a means for measurement of blood electrolytes and the blood gases of a patient during and after surgery, and even while in ambulatory transit. To provide that feature is another object of the invention.

Still another object is to provide a means for making multiple, periodic measurements using only a single access to the patient, such as an intravenous line, or any other access such as a needle, a catheter or a shunt between an artery and a vein.

Another object is to provide a method and apparatus which is convenient to use and sufficiently low in cost to permit disposal without loss of accuracy. In fact, one of the advantages of the invention is that it permits greater accuracy than is ordinarily obtained in tests conducted on drawn samples taken to a satellite or central clinical laboratory.

One feature of the invention is a novel mode of differential measurement. Another feature makes use of the apparatus employed in intravenous supply of fluids. Independently or combined with intravenous fluid therapy, substantial benefits are obtained. However, according to the invention, benefits are also obtained with measurements made in a non-differential mode.

In one sequence of a measurement cycle, an infusable, physiological calibrant solution is made to flow past the reference, ion selective, and gas sensing electrodes into the patient's blood stream. In this mode, the electrodes are calibrated. Periodically, the flow is reversed to draw blood into and up the intravenous line, past the in-line electrode module. In this mode measurement of the electrolytes and blood gases are made. The next mode is to return the blood to the patient, using a rapid flush, followed by a slow continuous flush with the same physiological calibrant solution whereby to keep the vein open.

In the differential mode, the reference electrode is separated from the electrode module to a location higher upstream. During the sampling cycle, the blood is drawn to immerse the sensing electrodes only, but not the reference electrode. Thus, the reference electrode is at all times exposed to the calibrant solution only. In this differential configuration, the "reference" electrode may be a simple chloridized silver wire or another ion selective electrode (ISE). Technically, a chloridized silver wire is also considered an ISE, as it is reversible to chloride ions. Chloride ions in the calibrant solution provide a stable reference potential.

Thus, there is no need to surround the reference electrode with a reference "filling" solution and a porous junction. The calibrant solution performs the function of "filling" solution as well. A section of tubing, filled with calibrant forms a liquid junction between the reference and the indicating sensing electrodes. In this configuration, where the reference electrode only sees the calibrant solution, be it the calibrate or measure mode, the residual liquid junction potential is eliminated, thereby providing a higher degree of accuracy.

In determinations of the chemistry of other fluids, urine for example, the flow direction of the fluid to be tested is reversed. A reference fluid is made to flow through a flow line from a source to a urine collection container past a reference electrode, and then past a series of selective measuring electrodes. Urine is removed from the subject's bladder and is flowed into the first mentioned flow line at a point downstream from the reference electrode and upstream from the selective measuring electrodes. During the calibration interval, urine flow is interrupted, the line is flushed with reference fluid, calibration is accomplished for each selective measuring electrode in turn, and the measurement is made. Reference fluid need flow only during calibration if the flow lines are arranged so that urine cannot reach the reference electrode. Measuring the amount of reference fluid that is flowed into the urine container is accomplished by measuring the reduction in volume in the reference fluid source container. By a simple subtraction, the amount of urine in the collection container is computed.

BRIEF DESCRIPTION OF THE DRAWINGS

In the drawings:

FIG. 1 depicts the apparatus in a preferred form of the invention, associated with an IV pole and an ambulatory patient, being used to measure the patient's blood chemistry periodically;

FIG. 2 is a schematic drawing of apparatus according to the invention used to measure the chemistry of a subject's urine;

FIG. 3 is a diagram, partially schematic and partially in block form, showing a generalized structural arrangement according to the invention;

FIG. 4 is a schematic view of a system according to the invention in which the blood chemistry measurement apparatus is not combined with apparatus for administering an IV fluid.

DESCRIPTION OF THE PREFERRED EMBODIMENT

Figure 5:
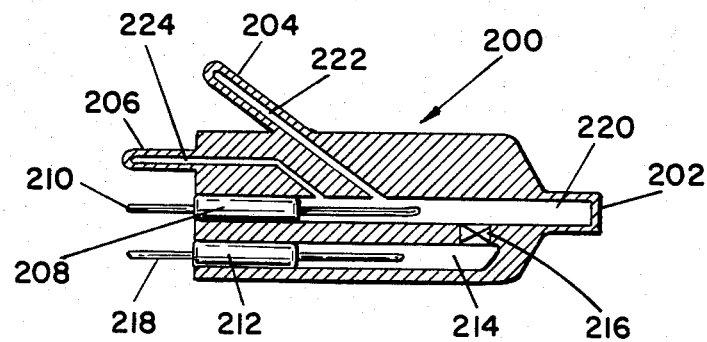
FIG. 5 is a diagram of an alternative form of sensor block.

The preferred embodiment of the invention utilizes an arrangement of ion selective electrodes and reference electrodes. Flow of calibrant and the fluid whose chemistry is to be tested is controlled according to the method of the invention. The method can be applied to a variety of circumstances. It can be used to measure the chemistry of blood when there is to be no loss of blood. It can be used to measure the chemistry of urine as urine is removed from the bladder. It can be used in consort with or without the flow of infusant to the blood, and it can be used to make measurements differentially or non-differentially. In the case of non-differential measurement, the electrodes are both subjected to a calibrant for calibration, and are both subjected to test fluid for measurement. In differential measurement, the reference electrode is subjected to calibrant both during calibration and measurement. The measuring electrode is subjected to calibrant during calibration, and it is subjected to test fluid during measurement.

The generalized structural arrangement is depicted in FIG. 3. To facilitate understanding of the generalized structure, two applications of the invention, both of which employ sub-sets of the generalized structure, are described. The first relates to measurement of blood chemistry in the circumstance in which some "IV fluid" is being infused into a subject's blood, and it is desired to employ a single needle to communicate with the patient's blood stream.

FIG. 1 is a view of a patient 10 with a portable stand 12, commonly called an IV pole because one of its primary uses is to hold elevated containers of material to be infused into a patient's bloodstream.

Pole 12 is applied to that use in FIG. 1. The infusant is contained in a bag 14 which hangs from arm 16 of the pole. The infusant flows by a flowpath, in this case conduit 18, to a flow pump and controller 20. Thereafter, it flows by a continuation of the flowpath in tube 22 past an analyzer instrument 24 to an electrode block 26. The block 26 is strapped to the patient's wrist. A tube 28 conducts fluid from block 26 to an intravenous needle 30.

A bottle 32 of a physiological calibration fluid hangs from arm 16 of the pole. Calibration fluid, often called reference fluid, is conducted to flow pump or controller 20 by a tube 36.

In the industry the term "controller" is used to designate a gravity fed drop counter. The term "pump" is used to designate a positive displacement feed structure. Pumps are generally more accurate than controllers, and are preferred.

The tube 22 in this embodiment is a three-lumen flexible tube. One lumen forms a continuation of the flowpath in conduit 18. It conducts infusant from the flow pump 20 to the electrode block 26. A capillary sized lumen in tube 22 conducts the reference or calibrant fluid to the electrode block 26 from the controller. Shielded electrode cables are threaded through the third lumen. They interconnect the electrodes in block 26 to the analyzer 24.

The analyzer 24 is a conventional instrument. It measures the electrical potential between an ion selective electrode and a reference electrode, and is available commercially in a variety of forms and with a variety of features. Analyzer 24 is capable of calibrating the electrodes and indicating pH and concentrations of calcium, potassium and sodium. It incorporates one feature that is non-standard. A switch 38 permits selection of either of two reference electrodes. In FIG. 1, the electrode block 26 houses a pH electrode, calcium, potassium and sodium ion selective electrodes, and two reference electrodes; one downstream from the ion selective means incorporates the materials of conventional reference electrodes. The other is an ion selective electrode positioned upstream from the measuring electrode to permit practice of a novel method of measurement here called differential measurement.

The analyzer shown is programmable to make its measurements in a predefined sequence automatically or in response to a triggering signal.

The pump 20 is also a standard unit, one of several commercially available. While they vary in the specifics of their construction and the number of fluid lines controlled, all include a timer and a fluid metering pump.

The pump shown employs peristaltic metering pumps, one for each of two lines. When the pump stops, it serves as a closed valve. The timer is programmable and, in this case, is programmed to interrupt the supply of infusant periodically for a short measurement interval.

An apparatus for measuring the chemistry of urine is shown schematically in FIG. 2. A catheter 40 removes urine from a subject's bladder 42. The urine passes through a shut-off valve 44 as it flows down flow tube 46 to a junction at 48 with the flow tube 50 for calibrant. The calibrant is contained in a container 52 from whence it passes through pump 54 and valve 56. In this case, a positive displacement pump is employed. The same structure serves as pump and valve. The calibrant then flows toward the junction 48. The reference electrode 58 is subjected to the calibrant upstream from junction 48 and, therefor, is never subjected to urine. Below the junction, the urine and calibrant flow in the same tube 60 which contains a sensor block 62. Here, ion selective sensors measure selected chemical constituents of the flow. The sensor outputs are analyzed and converted to readable form in the analyzer 64. The urine and calibrant are collected in a container 66 where the quantity of urine collected is calculated by subtracting the volumetric reduction in the calibrant container from the total volume collected.

The control unit 68 in FIG. 2 controls operation of valves 44 and 56 and pump 54 and, as before, where the pump generally designated 69 is a positive displacement unit, it performs the valve function and the valves, pump. and controller are conventionally called a "pump."

The preferred method of the invention involves flowing a calibrant solution through a conduit in which at least one reference electrode and at least one ion selective electrode are incorporated. The ion selective electrode is calibrated while the electrodes are subjected simultaneously to only the calibrant solution. Then the flow is altered to subject the ion selective electrode to the fluid whose chemistry is to be measured. If measurement is to be made in the differential mode, that alteration of flow is such that only the ion selective electrode, and not the reference electrode, is subjected to the test fluid. In the differential mode, the reference electrode is subjected only to the calibrant. If the measurement is to be made in the more common non-differential mode, both the ion selective electrode and the reference electrode are subjected to test fluid during the measurement.

When measuring blood chemistry, the preferred method includes injecting a hollow needle into a blood vessel. The needle is connected to the flowpath for calibrant. When the measurement is made, flow is altered to withdraw blood into the flowpath until the ion selective electrode, or electrodes are subjected to it. When the measurement has been made, flow is reversed and the blood is returned to the vessel along with calibrant fluid. Because the flow rate and volume of calibrant fluid are very low, it is not essential to discontinue flow of calibrant between measurements when the frequency of measurement is relatively high.

If another fluid is to be infused into the subject's blood stream during the course of blood chemistry measurement, it is possible to use a single needle to perform both tasks. The infusant is caused to flow using a conventional pump and pump controller. Periodically, the flow of infusant is interrupted and flow direction is reversed to draw blood through the needle into contact with the ion selective electrodes. In the special circumstance in which the infusant contains known quantities of the substances to which the ion selective electrodes are selective, the infusant can serve as the calibrant.

When the fluid to be measured is urine or anything else that is removed from the subject, the flow direction is reversed. It flows from the subject to a collection container. Thus, in the case of urine, urine is taken from the subject through a catheter. It flows through a flowpath past the ion selective electrodes and, in the case of non-differential measurement, past the reference electrode. If differential measurement is preferred, the reference electrode is mounted in the flowpath for calibrant upstream from the junction of the calibrant and urine flowpaths. The measuring electrodes are mounted downstream from the junction. When the electrodes are to be calibrated, urine flow is interrupted. When the urine chemistry is to be measured, the flow of calibrant is interrupted. The generalized structure is depicted in FIG. 3.

The sensor block 100 includes a flowpath 102 for calibration fluid, a flowpath 104 for another fluid such as urine or an "IV fluid" to be infused into a patient's blood stream, a third flowpath 106 extends from the junction 108 of flowpaths 102 and 104 to outlet 110. A conduit 112 leads from the outlet to a needle 114. The needle would be removed and replaced with a receiving container if the fluid to be measured was urine or some industrial fluid not to be returned to the source.

An upstream reference electrode 116 has its sensing portion disposed in calibrant flowpath 102. A second reference electrode 118 is a conventional one in which the sensing elements are immersed in a body of salt solution 120 such as KCL which is separated from the flowpath 106 by a salt bridge 122. Electrodes 124, 126, 128 and 130 are ion selective electrodes for measuring concentrations of $K^+$, $Na^+$ and $Ca^{++}$ and pH, respectively.

The connection wires of these several ion selective electrodes and that of a color sensor set are connected to a conventional electrode voltage analyzer 140. The color sensor is numbered 134. Its function is to sense when blood has reached a level above all of the ion sensitive electrodes during measurement of blood chemistry. In practice, the color sensor may be omitted if the pumps are positive displacement units.

The "pump" 142 is a conventional two circuit positive displacement pump in the preferred embodiment. It includes two peristaltic pumps and a timer and electronic means for interrelating pump and timer. Functionally, it includes the controller and timer CONT 146, a pump 148 and valve 150 associated with fluid line 152, and a pump 154 and valve 156 in calibrant fluid line 158. Both pumps are reversible.

Line 152 connects to line 104 of the sensor block 100 and line 158 connects to line 102 of the sensor block. Line 152 extends from the outlet of a fluid container 160 which corresponds to the IV fluid container 14 in FIG. 1 or to the bladder 42 in FIG. 2, or to some other source of fluid whose chemistry is to be measured according to the method for urine. Line 158 connects to the outlet of a calibrant container 162. Container 162 corresponds to container 32 of FIG. 1 or container 52 of FIG. 2. Analyzer 140 corresponds to analyzers 24 and 64 in FIGS. 1 and 2, respectively. Also, the pump 142 of FIG. 3 corresponds to pumps 20 and 69 of FIGS. 1 and 2, respectively.

The sensor block 26 of FIG. 4 is the same as sensor block 26 of FIG. 1. Its second, non-differential mode calibration electrode is a pH electrode in this case. It may be located at any level in the common flowpath. It corresponds to calibration electrode 67 in FIG. 2. In FIG. 2, the upstream reference electrode 58 corresponds to upstream reference electrode 116 in FIG. 3. Its specific location can be anywhere in the calibrant fluid line, but, for convenience, the arrangement of FIG. 3 is preferred.

The operation of the apparatus of FIG. 4 is described as follows, the assumption being made that needle 114 is inserted into a patient's blood vessel and that container 162 contains a calibrant. When it is desired to measure blood chemistry, pump 154 and valve 156 is opened. Calibrant is pumped through flowpaths 158 and 112 and through the needle 114. Enough is pumped to insure that the ion selective electrodes and the two reference electrodes are subjected to calibrant. The analyzer 140 is set to calibrate either one of the reference electrodes and the ion selective electrodes, depending upon whether differential or non-differential measurement is desired. If both are desired, the ion selective electrodes are calibrated against one of the reference electrodes. The measurement is then taken and the process is repeated for the other reference electrode.

The measurement is taken by reversing pump 154 to draw blood up through the needle 114 and flowpaths 112 and 156 to a point just past the ion selection electrodes.

The signals from the ion selective sensors, now subjected to blood, are supplied to the analyzer 140 where the amount of the materials sensed is calculated. The calculation having been made, pump 154 is again reversed. The small quantity of blood in the needle 114 and flowpaths 112 and 158 is returned to the patient's blood vessel and then the pump is stopped and valve 154 is closed, or the valve is left open and pumping is continued at a very low rate to keep the vessel open, until the next measurement is to be made.

A major advantage of the invention lies in the fact that the upstream reference electrode can be any ion selective electrode or even as simple as a chloridized silver wire when measuring the chemistry of fluids whose chemistry is approximately known. A calibrant such as a modified and buffered Ringer solution is formulated to have sodium, potassium, calcium, chloride and a fixed, buffered pH in the physiological range. The upstream reference electrode sees the same concentration of $Cl^-$ ions in the calibrant at all times. Therefore, without using the conventional KCl and salt bridge, it will always provide the same reference potential as long as it is not subjected to the test fluid. The chloridized silver wire serves as an ion selective electrode selective to the $Cl^-$ ion. The mere fact that the upstream electrode always sees the calibrant and never sees the test fluid means that the measurement is made in the differential mode.

If non-differential measurement is not required, the downstream reference electrode is simply omitted. In that case, there is no fluid in the sensor block. It can be stored dry. On the other hand, it is often possible to employ a pH electrode using a glass electrode as the non-differential mode reference electrode. Such electrodes are sealed against evaporation of their reference fluid.

In a typical case, the pump 154 would be set to pump calibrant from reservoir 162 to the needle 114 and into the patient at the rate of 1 milliliter per minute for fifteen seconds. During that time, the ion selective electrodes are calibrated. Then pump flow is reversed to withdraw blood until it reaches the ion selective electrodes in block 26, but not the reference electrode 116. The assumption is made that the measurement is to be made in the differential mode. The measurement is completed within five seconds. The pump direction is then reversed and the blood is flushed back into the patient at the rate of one mililiter per minute for fifteen seconds. Thereafter, the pump rate is slowed to the rate of ten microliters per minute to keep the blood vessel open.

In this method, the amount of calibrant required is very small. Thus, it permits frequent monitoring of blood chemistry without interferring with fluid therapy if any. Moreover, the apparatus for this method is easily portable.

Another form of sensor block is illustrated in FIG. 5. It is arranged for non-differential measurement. The block is numbered 200, the outlet 202 is sealed closed. So are the two inlets. The inlet 204 is used to introduce calibrant if another fluid, urine or IV fluid, is to be introduced at inlet 206. If there is no second fluid, either inlet may be used to introduce calibrant.

The ion selective electrode 208 is molded in situ. It is fitted with an external connector pin 210. The reference electrode 212 and a body 214 reference material in jel form are molded in the body along with a salt bridge or porous junction 216. Electrode 212 has an external connection pin 218.

When the sensor block is to be used, the tip of outlet 202 is cut off to reveal the inner flowpath 220. The tip of one or both of the inlets 204 are cut off to afford access to flowpaths 222 and 224, respectively, as required.

Although I have shown and described certain specific embodiments of my invention, I am fully aware that many modifications thereof are possible. My invention, therefore, is not to be restricted except insofar as is necessitated by the prior art.

I claim:

1. The method of measuring a chemical property of a body fluid using a conduit which terminates in a quantity of the body fluid and which incorporates a first electrode selective to said property and a second, reference electrode at spaced points along its length, which method comprises the steps of:

filling said conduit with a quantity of reference fluid sufficiently to subject both of said electrodes to the reference fluid; and at another time, filling said conduit with a quantity of the reference fluid such that the reference electrode is subjected to reference fluid, and with a quantity of the body fluid such that the first electrode is subjected to the body fluid.

2. The method defined in claim 1 in which the conduit is filled with reference fluid by flowing the reference fluid through the conduit past the first and second electrodes in the direction toward said quantity of body fluid, and thereafter reversing flow in said conduit such as to withdraw body fluid from said quantity of blood to a point in said conduit intermediate said first and second electrodes.

3. The invention defined in claim 1 in which the step of filling the conduit with a quantity of reference fluid and blood is accomplished by reversing the flow of reference fluid in said conduit and aspirating body fluid along the conduit to fill the conduit with body fluid from said quantity of body fluid to a point along said conduit between said electrodes.

4. The invention defined in claim 3 in which the body fluid is blood and which method comprises the further step of flowing an infusant into said quantity of blood and of interrupting the flow of infusant whenever blood is aspirated along said conduit.

5. The invention defined in claim 4 which comprises the step of interrupting flow of reference fluid in said conduit during intervals in which infusant is flowing into said quantity of blood.

6. The invention defined in claim 3 in which said conduit incorporates a plurality of ion selective electrodes at a point intermediate said quantity of body fluid and said reference electrode, each of said ion selective electrodes being selective to a different ion; and
    said body fluid being aspirated into said conduit such that each of said electrodes other than said reference electrode is subjected to the body fluid.

7. The method of measuring blood chemistry using an apparatus comprising a calibratable electrode signal measuring unit, a source of reference fluid, connection means for completing a connection to the bloodstream of a subject, an electrode set having a reference electrode and at least one ion selective electrode, and a flowpath extending from said connection means to said source and in which said electrodes are exposed, said method comprising the steps of:
    (a) connecting said connection means to the bloodstream of a subject;
    (b) flowing reference fluid from said source through said flowpath past said electrodes and into the bloodstream of the subject such that said electrodes are subjected simultaneously to said reference fluid;
    (c) calibrating said measuring unit while the electrodes are subjected to reference fluid;
    (d) thereafter, reversing flow in said flowpath such that blood from said bloodstream is drawn into said flowpath and reference fluid is returned to said source until at least said ion selective electrode is subjected to blood from said bloodstream;
    (e) making a measurement with said measuring unit while said ion selective unit is subjected to said blood; and
    (f) again reversing the direction of flow in said flowpath to return all of the blood withdrawn from said bloodstream and to cause a flow of reference fluid past said electrodes into said bloodstream.

8. The method of measuring blood chemistry using an apparatus comprising a calibratable electrode signal measuring unit, a source of reference fluid, connection means for completing a connection to the bloodstream of a subject, an electrode set having a reference electrode and at least one ion selective electrode, a first flowpath extending from said connection means to said source and in which said electrodes are exposed, a source of intravenous fluid and a second flowpath interconnecting said source of intravenous fluid with said first flowpath at a point in said first flowpath between said source of reference fluid and said electrode set, said method comprising the steps of:
    (a) connecting said connection means to the bloodstream of a subject;
    (b) flowing reference fluid from said source through said first flowpath past said electrodes and into the bloodstream of the subject such that said electrodes are subjected simultaneously to said reference fluid;
    (c) calibrating said measuring unit while the electrodes are subjected to reference fluid;
    (d) thereafter, reversing flow in at least one of said flowpaths such that blood from said bloodstream is drawn into said flowpath and fluid is returned to at least one of said sources until said ion selective electrode is subjected to blood from said bloodstream;
    (e) making a measurement with said measuring unit while said ion selective unit is subjected to said blood; and
    (f) again reversing the direction of flow in said flowpath to return all of the blood withdrawn from said bloodstream and to cause a flow of reference fluid past said electrodes into said bloodstream.

9. Apparatus for measuring blood chemistry comprising:
    (a) a calibratable electrode signal measuring unit;
    (b) a source of reference fluid;
    (c) connection means for completing a connection to the bloodstream of a subject;
    (d) an electrode set having a reference electrode and at least one ion selective electrode;
    (e) a flowpath extending from said connection means to said source and in which said electrodes are exposed; and
    (f) means for causing reference fluid to flow from said source through said flowpath past said electrodes and into the bloodstream of the subject such that said electrodes are subjected simultaneously to said reference fluid and for calibrating said measuring unit while the electrodes are subjected to reference fluid and thereafter reversing flow in said flowpath such that blood from said bloodstream is drawn into said flowpath and reference fluid is returned to said source until at least said ion selective electrode is subjected to blood from said bloodstream.

10. Apparatus for measuring blood chemistry comprising:
    (a) a calibratable electrode signal measuring unit;
    (b) a source of reference fluid;
    (c) a source of intravenous fluid;
    (d) connection means for completing a connection to the bloodstream of a subject;
    (e) an electrode set having a reference electrode and at least one ion selective electrode;
    (f) a first flowpath extending from said connection means to one of said sources and in which said electrodes are exposed; and
    (g) a second flowpath interconnecting the other of said sources with said first flowpath at a point in said first flowpath between said one source and said electrode set; and
    (h) means for causing reference fluid to flow from one of said sources through said flowpath past said electrodes and into the bloodstream of the subject such that said electrodes are subjected simultaneously to said reference fluid and for calibrating said measuring unit while the electrodes are subjected to reference fluid and thereafter reversing flow in said flowpath such that blood from said bloodstream is drawn into said flowpath and fluid is returned to at least one of said sources until at least said ion selective electrode is subjected to blood from said bloodstream.

* * * * *